United States Patent [19]

Fertel et al.

[11] Patent Number: 5,059,697
[45] Date of Patent: Oct. 22, 1991

[54] PREPARATION OF HALOGENATED PHTHALIC ANHYDRIDES

[75] Inventors: Lawrence B. Fertel, Buffalo; Neil J. O'Reilly; Henry C. Lin, both of Grand Island, all of N.Y.

[73] Assignee: Occidental Chemical Corporation, Grand Island, N.Y.

[21] Appl. No.: 537,717

[22] Filed: Jun. 14, 1990

[51] Int. Cl.$^5$ .................. C07D 307/77; C07D 307/36
[52] U.S. Cl. .................... 549/246; 549/240; 549/262
[58] Field of Search ................ 549/240, 246, 262

[56] References Cited

U.S. PATENT DOCUMENTS

| | | | |
|---|---|---|---|
| 4,560,772 | 12/1985 | Telschow et al. | 549/240 |
| 4,560,773 | 12/1985 | Telschow et al. | 549/247 |
| 4,684,737 | 8/1987 | Horino et al. | 549/246 |
| 4,709,056 | 11/1987 | Cotter et al. | 549/246 |
| 4,978,760 | 12/1990 | Spohn | 549/246 |

FOREIGN PATENT DOCUMENTS

| | | | |
|---|---|---|---|
| 135153 | 3/1985 | European Pat. Off. | 549/240 |
| 330219 | 8/1989 | European Pat. Off. | 549/246 |
| 334049 | 9/1989 | European Pat. Off. | 549/246 |
| 338215 | 10/1989 | European Pat. Off. | 549/246 |
| 1171477 | 8/1986 | Japan | 549/240 |

OTHER PUBLICATIONS

Ohkatsu et al., J. Japan Petrol. Inst. 164-9(1979).
Skvarchenko, Russian Chemical Reviews, vol. 32, pp. 571-589 (1963).
Peter P. Fu et al., Chemnical Review, vol. 78, No. 4, p. 317 (1978).
N. I. Shuiken et al. CA 60-14401b (1964).
N. I. Shuiken et al., CA 55-17547g (1961).
Oseledchik et al., Izv. Akad. Nauk. SSSR. Ser. Khim., 6, 1315 (1973).
March, Advanced Org. Chem. 3rd Edition pp. 1052-1054.
Bergmann; JACS, vol. 64, p. 176 (1942).

*Primary Examiner*—Cecilia Shen
*Attorney, Agent, or Firm*—James F. Tao; John H. Engelmann

[57] ABSTRACT

A process for the aromatization of 4-chlorotetrahydrophthalic anhydride and 4,5-dichlorotetrahydrophthalic anhydride which comprises heating a solution of either substance in the presence of activated carbon and in the partial absence of air.

9 Claims, No Drawings

PREPARATION OF HALOGENATED PHTHALIC ANHYDRIDES

BACKGROUND OF THE INVENTION

This invention relates to a process for the aromatization of chlorotetrahydrophthalic anhydrides to form chlorophthalic anhydrides. Substituted phthalic anhydrides are valuable raw materials for the synthesis of useful products. These anhydrides are utilized as intermediates in the synthesis of organic polymers, particularly polyimides, dyes, plasticizers, and in other uses.

Procedures are known for preparing substituted phthalic anhydrides. U.S. Pat. No. 4,560,772 discloses the reaction of 4-methyltetrahydrophthalic anhydride with excess sulfur and a catalytic amount of zinc oxide and 2-mercaptobenzothiazole to produce 4-methylphthalic anhydride and hydrogen sulfide.

U.S. Pat. No. 4,560,773 discloses a similar reaction between the electron-rich 4-methyl-tetrahydrophthalic anhydride and bromine in the presence of a catalytic amount of an acid acceptor such as dimethylformamide or pyridine in the liquid phase.

U.S. Pat. No. 4,709,056 discloses the dehydrohalogenation of 4-halo-4-flourohexahydrophthalic anhydrides through the use of a basic alumina catalyst in a liquid phase to produce two isomers of 4-fluorotetrahydrophthalic anhydride. The patent further discloses that the mixture of the isomers or the separate isomers may be dehydrogenated to fluorophthalic anhydride using a palladium on a carbon catalyst.

Ohkatou et al, Sekiyu Gakkasishi 1979, 22(3), (J. Japan Petrol. Inst.,) 164–9 (1979) (CA 91:74241e) discloses the dehydrogenation of hydrocarbons using an activated carbon bed to produce the corresponding olefins. The mechanism of the reaction using cyclohexane and cyclohexene were studied using a pressure flow technique.

Bergmann, J. Amer. Chem. Soc., 64, 176 (1942) discloses the aromatization of tetrahydrophthalic anhydride products of Diels-Alder reactions. The author discloses that dehydrogenation occurs when the tetrahydrophthalic anhydride product is boiled in nitrobenzene. However, it is further disclosed that dehydrogenation does not occur when p-bromonitrobenzene, p-chloronitrobenzene, or m-dinitrobenzene in xylene is employed. Moreover, it has been shown in our laboratories that when the halotetrahydrophthalic anhydrides of this publication are dehydrogenated in nitrobenzene, a portion of the nitrobenzene is reduced to aniline. The aniline reacts with the anhydride group of either the starting material or product to form imides and thus lower the yield of desired product.

Skvarchenko et al, Obschei Khimii, Vol. 30, No. 11, pp 3535–3541 (1960) disclose the aromatization of chloro-substituted tetrahydrophthalic anhydride by heating with phosphorus pentoxide. In the aromatization process described however, decarboxylation also occurs with the formation of the corresponding chloro-substituted benzene compound. The preparation of tetrahydrophthalic acids and anhydrides and various methods for dehydrogenation and aromatization thereof are reviewed by Skvarchenko in Russian Chemical Reviews, November 1963, pp 571–589.

P. P. Fu and R. G. Harvey disclose in Chem. Rev. 1978, 78 (4), 317 that platinum and palladium either as finely divided free metals or supported on activated carbon, are the most generally satisfactory catalysts for the dehydrogenation of hydroaromatic compounds. Attempts were made in our laboratories to use palladium on carbon as a catalyst for the aromatization of the halotetrahydrophthalic anhydride of this invention. The expected aromatization did occur; however, the catalyst also produced hydrodechlorination and the product produced was contaminated with significant phthalic anhydride or monochlorophthalic anhydride. Similar results were obtained with platinum or rhodium catalysts.

The published European patent application EP 89 10 3248.84, (European Patent 330,219) discloses a process for the aromatization of 4-chloro-tetrahydrophthalic anhydride in the presence of air and activated carbon to form 4-chlorophthalic anhydride. The process may be conducted in the vapor phase in the range of 200° to 400° C., or in solution from 200° to 300° C. Having the proper amount of air in the reaction is important because the oxygen in the air unites with the hydrogen atoms removed in the aromatization reaction to form water. When the reaction is run in solution, the water produced must be removed since it is known that water hydrolyzes phthalic anhydrides leading to reduced yields.

SUMMARY OF THE INVENTION

Surprisingly, we have now discovered that 4-chlorotetrahydrophthalic anhydride and 4,5-dichlorotetrahydrophthalic anhydride may be aromatized by heating a solution of either substance in the presence of activated carbon and in the partial absence of air.

DETAILED DESCRIPTION OF THE INVENTION

The present invention provides a process for aromatizing 4,5-dichlorotetrahydrophthalic anhydride to form 4,5-dichlorophthalic anhydride and 4-chloro-tetrahydrophthalic anhydride to form 4-chlorophthalic anhydrides. The desired aromatization is accomplished by heating the halotetrahydrophthalic anhydride in a high boiling solvent in the presence of an activated carbon catalyst.

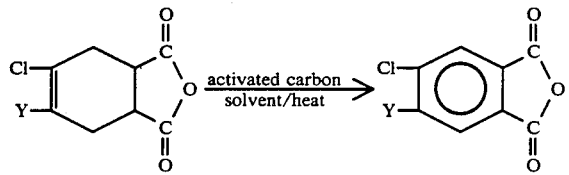

where Y is H or Cl.

The starting tetrahydrophthalic anhydrides are known compounds and may be prepared by the Diels-Alder addition of 2-chlorobutadiene or 2,3-dichlorobutadiene with maleic anhydride. The process of the present invention may be conducted in any solvent which is stable at the temperatures involved in this process, and in which the tetrahydrophthalic anhydride is sufficiently soluble. High boiling, saturated hydrocarbons such as decane, and chlorinated solvents such as chloro-decanes and chloro-octane are suitable solvents. High boiling polyethers, which have been carefully dried, such as diethylene glycol diethyl ether, and similar compounds, are also suitable solvents. The preferred solvents are halogenated aromatics such as 1,2,4-trichlorobenzene.

The reaction may be run within a wide temperature range. Reactions conducted at higher temperature proceed more quickly, but may produce side products. A practical temperature range in which to run the reaction is from about 185° to about 300° C. If the reaction is run at higher temperatures, higher boiling solvents are required, or it is necessary to run the reaction under pressure. The preferred temperature range for the reaction is from about 185° to about 195° C.

Although no attempt is made to exclude oxygen from the reaction mixture, the process is such that oxygen is at least partially excluded. At the temperatures at which this reaction is conducted, the organic solvent volatilizes and displaces much of the air which was initially present in the reaction vessel. The heating of the solvent serves to partially exclude air from the reaction and the closer the reaction temperature is to the boiling point of the solvent, the more air is excluded from the reaction. In addition, air is not particularly soluble in the organic solvents used to conduct this reaction, especially at high temperatures. Accordingly, the air which may be present above the reaction mixture does not readily go into solution. Thus, there is no oxygen in the solution to react with the hydrogen which is removed during the aromatization process. The lack of oxygen in the reaction is illustrated by the fact that water is not observed as a product of the reaction.

Water is known to react with phthalic anhydride. In any higher temperature reaction in which a phthalic anhydride is a desired product, the presence of water can reduce yields by hydrolysis to the phthalic acid and subsequent decarboxylation to a benzoic acid at the elevated reaction temperature. Accordingly, in such reactions, steps are generally taken to remove water, or control its reactivity in some way. It is a particular advantage of the process of the current invention that water is not produced and, accordingly, the processing is simpler because no steps are required to control or remove the water from the product mixture.

Solvent volatilization is not the only method which may be used to exclude air. For example, air may be fully excluded using an inert atmosphere over the surface of the reaction to exclude air, or bubbling an inert gas through the reaction mixture to exclude air. The partial exclusion of air provided by the volatilization of hot organic solvents is generally appropriate for the process of this invention. However, the higher degrees of exclusion created by methods such as bubbling an inert gas through the reaction mixture are not detrimental to the process. Accordingly, the process may be run with at least partial exclusion of the air or such greater degree of exclusion as may be convenient.

Typically, the amount of activated carbon used in this reaction is between about 10 and 50% of the weight of chlorotetrahydrophthalic anhydride used. The preferred amount of activated carbon ranges from about 20 to 30% of the weight of chlorotetrahydrophthalic anhydride. The reaction is generally complete in about 20 to 30 hrs and the product is recovered by filtration followed by cooling of the solution. It is an advantage of the process of the present invention is that the impurities which may be formed are likely to be absorbed by the activated carbon and, accordingly, the product which crystallizes from the reaction mixture is extremely pure.

The following specific examples are provided to further illustrate this invention and the manner in which it may be carried out. It will be understood, however, that the specific details given in the example have been chosen for purposes of illustration, and are not to be construed as limitations on the invention.

EXAMPLE 1

Preparation of 4,5-dichlorophthalic anhydride

A mixture of 5.0 grams (22.7 mmol) of 4,5,-dichlorotetrahydrophthalic anhydride and of activated carbon (Darco KB-60, 1.0 gram) was slurried with 10 mL of 1,2,4-trichlorobenzene and heated to 190° C. for 25 h. The reaction mixture was then filtered while hot and the filtrate was allowed to cool to room temperature, at which time the product precipitated out of solution. After the addition of 5 mL of hexanes to ensure complete precipitation, the product was collected and washed with hexanes. Drying in a vacuum dessicator (60° C., 0.25 mm Hg, 24 h) gave 1 (3.9 g, 80% yield, 99.6% purity by GC), mp 185°–16.5° C. (lit mp 187° C.).

EXAMPLE 2

Preparation of 4-chlorophthalic anhydride

A reaction flask was charged with 1.97 g of 4-chlorotetrahydrophthalic anhydride and 0.98 g of activated carbon (DARCO KB-60). 1,2,4-trichlorobenzene (15 mL) was added and the reaction heated to 190° C. Analysis of the reaction mixture showed the formation of 4-chlorophthalic anhydride, with no phthalic anhydride formed at all.

EXAMPLE 3

Preparation of 2,3-dichlorobutadiene from meso-1,2,3,4-tetrachlorobutane

A 1 L, 3-neck, round bottom flask equipped with a thermometer and a stir bar was charged with 64 g of potassium hydroxide and 220 mL of methanol. The solution was cooled to 10° C., at which time a solution of the starting material (100 g) in methanol (50 mL) was added, at such a rate that the temperature never exceeded 20° C. After addition, the temperature was warmed to 25° C., and the reaction was allowed to stir for 2 h. The solution was filtered to remove the precipitated potassium chloride, and poured onto 1.5 L of water. The product was separated, dried and distilled to give 34.5 g (55%) of 2,3-dichlorobutadiene at 97% purity.

EXAMPLE 4

Preparation of 2,3-dichlorobutadiene from 2,3,4-trichloro-1-butene

A 1 L, 3-neck, round bottom flask equipped with a thermometer and a stir bar was charged with 64 g of potassium hydroxide and 200 mL of methanol. The solution was cooled to 10° C., at which time the starting material (158 g) was added, at such a rate that the temperature never exceeded 20° C. After addition, the temperature Was Warmed to 25° C., and the reaction was allowed to stir for 2 h. The solution was filtered to remove the precipitated potassium chloride, and poured onto 1 L of water. The product was separated, dried and distilled to give 85.2 g (55%) of 2,3-dichlorobutadiene.

EXAMPLE 5

Diels-Alder reaction of 2,3-dichlorobutadiene with maleic anhydride

A 500 mL reaction flask was charged with 34.5 g of 2,3-dichlorobutadiene and 27.5 g of maleic anhydride. 200 mL of toluene was added, along with a small amount of BHT (0.5 g). The solution was heated to reflux until the reaction was complete. The toluene was removed and the product recrystallized from ethyl acetate/hexanes to give 38.25 g (61.8%) of 4,5-dichlorotetrahydrophthalic anhydride.

We claim:

1. A process for the preparation of a halogen-substituted phthalic anhydride of the formula

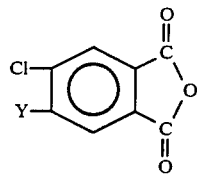

where Y is either hydrogen or chlorine, by heating a halogen substituted tetrahydrophthalic anhydride of the formula

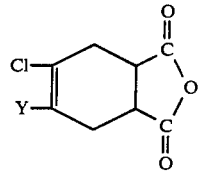

where Y is either hydrogen or chlorine, in a liquid phase, with at least partial exclusion of air in the presence of activated carbon.

2. A process according to claim 1 conducted at a temperature of about 185° to 300° C.

3. A process according to claim 2 conducted at a temperature of about 185° to 195° C.

4. A process according to claim 2 wherein the halogen substituted tetrahydrophthalic anhydride is 4-chlorotetrahydrophthalic anhydride.

5. A process according to claim 4 wherein said 4-chlorotetrahydrophthalic anhydride is prepared by the Diels-Alder addition of 2-chlorobutadiene to maleic anhydride.

6. A process according to claim 4 conducted at a temperature of about 185° to 195° C.

7. A process according to claim 2 wherein the halogen substituted tetrahydrophthalic anhydride is 4,5-dichlorotetrahydrophthalic anhydride.

8. A process according to claim 6 conducted at a temperature of about 185° to about 195° C.

9. A process according to claim 8 wherein said 4,5-dichlorotetrahydrophthalic anhydride is prepared by the Diels-Alder addition of 2,3-dichlorobutadiene to maleic anhydride.

* * * * *